United States Patent
Satou et al.

(10) Patent No.: US 12,322,516 B2
(45) Date of Patent: Jun. 3, 2025

(54) STORAGE MEDIUM AND CASE SEARCH APPARATUS

(71) Applicant: Konica Minolta, Inc., Tokyo (JP)

(72) Inventors: Ken Satou, Mitaka (JP); Sumiya Nagatsuka, Hino (JP); Ikki Nakamura, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 351 days.

(21) Appl. No.: 17/884,211

(22) Filed: Aug. 9, 2022

(65) Prior Publication Data

US 2023/0059667 A1    Feb. 23, 2023

(30) Foreign Application Priority Data

Aug. 17, 2021 (JP) ................... 2021-132708

(51) Int. Cl.
| | |
|---|---|
| *G06T 7/00* | (2017.01) |
| *G06F 16/532* | (2019.01) |
| *G06V 10/22* | (2022.01) |
| *G06V 10/74* | (2022.01) |
| *G16H 50/70* | (2018.01) |

(52) U.S. Cl.
CPC ............ *G16H 50/70* (2018.01); *G06F 16/532* (2019.01); *G06V 10/235* (2022.01); *G06V 10/761* (2022.01)

(58) Field of Classification Search
CPC .. G06F 16/532; G16H 50/70; G06K 9/00778; G06Q 30/0252; G06T 7/593; H04N 13/128; H04N 13/271
See application file for complete search history.

(56) References Cited

U.S. PATENT DOCUMENTS

2021/0248769 A1* 8/2021 Luo ................... G06T 7/593

FOREIGN PATENT DOCUMENTS

| JP | 2007-279942 A | 10/2007 |
|---|---|---|
| JP | 2013-081579 A | 5/2013 |
| JP | 2019-063328 A | 4/2019 |
| JP | 2021-087464 A | 6/2021 |
| WO | 2013/001678 A1 | 1/2013 |

OTHER PUBLICATIONS

Notice of Reasons for Refusal issued in corresponding Japanese Patent Application No. 2021-132708, mailed Apr. 1, 2025, with translation (15 pages).

* cited by examiner

*Primary Examiner* — Phuoc H Doan

(74) *Attorney, Agent, or Firm* — Osha Bergman Watanabe & Burton LLP

(57) ABSTRACT

A non-transitory computer-readable storage medium storing instructions causing a computer of a case search apparatus to: execute a case search using a dynamic image, and output at least one of a similar case image similar to the dynamic image and a case candidate related to the dynamic image.

25 Claims, 7 Drawing Sheets

STORAGE MEDIUM AND CASE SEARCH APPARATUS

CROSS-REFERENCE TO RELATED APPLICATIONS

The entire disclosure of Japanese Patent Application No. 2021-132708 filed on Aug. 17, 2021 is incorporated herein by reference.

BACKGROUND

Technical Field

The present invention relates to a storage medium and a case search apparatus.

Description of Related Art

Conventionally, when searching for similar cases using a search apparatus that searches for cases, the doctor first checks the patient information, such as the chief complaint and patient accompanying information of the relevant patient, and objective information based on the examination images taken. When the doctor inputs the patient's symptom and possible disease name as keywords into the search apparatus, the search apparatus performs a search based on the input keywords. In such a keyword search, there is a possibility that the cases retrieved will vary depending on the type of keywords considered by the doctor and the doctor's skill in deciphering symptoms.

In this connection, JP 2007-279942 A describes a similar case search apparatus that performs machine learning of the feature amounts obtained from the case image and the diagnosis result of the case image, and searches for case images similar to the diagnosis target image on the basis of the feature amounts obtained from the diagnosis target image.

However, the medical images that are the case images and the diagnosis target image described in JP 2007-279942 A are still images. Since the amount of information contained in still images is less than that contained in dynamic images, which are moving images, searches using still images in search apparatus may be less accurate than searches using moving images.

SUMMARY

One or more embodiments of the present invention provide a technological improvement over conventional storage mediums and case search apparatuses. For example, one or more embodiments provide a storage medium for instructions and a case search apparatus that can perform more accurate search, which provides a practical and technological improvement over conventional storage mediums and case search apparatuses.

According to an aspect of the present invention, a non-transitory computer-readable storage medium stores instructions causing a case search apparatus to execute a case search, the instructions causing a computer of the case search apparatus to: execute a search using a dynamic image, and output at least one of a similar case image similar to the dynamic image and a case candidate related to the dynamic image.

According to another aspect of the present invention, a case search apparatus comprises a hardware processor that executes a search using a dynamic image, and outputs at least one of a similar case image similar to the dynamic image and a case candidate related to the dynamic image.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, embodiments according to the present invention will be described with reference to the drawings. However, the scope of the invention is not limited to the disclosed embodiments or illustrated examples.

[Configuration of Case Search System 100]

Figure 1:
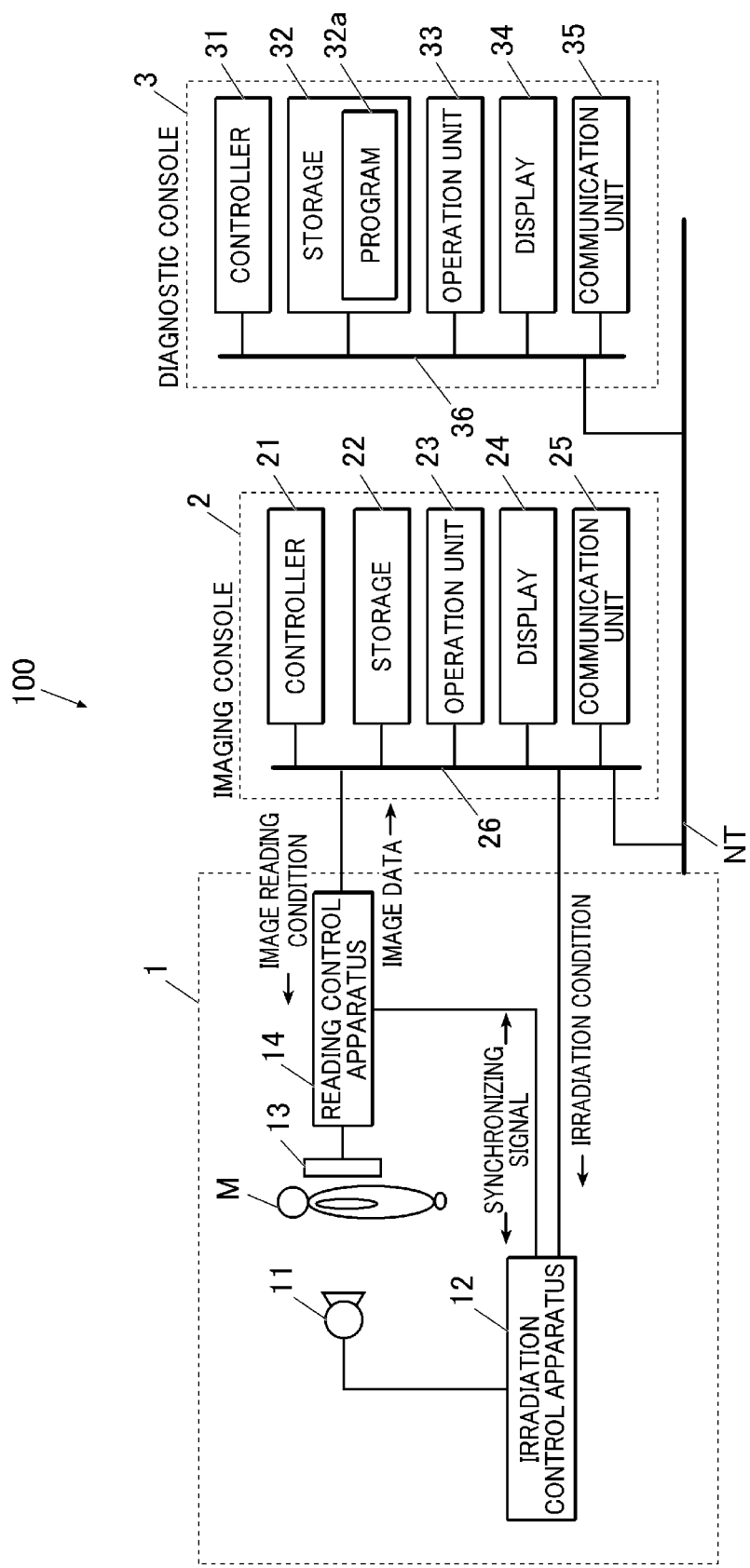
FIG. 1 is a view showing the entire configuration of a case search system in one or more embodiments of the present invention.

FIG. 1 shows the entire configuration of a case search system 100 in one or more embodiments.

As shown in FIG. 1, the case search system 100 is configured by connecting an imaging apparatus 1 to an imaging console 2 via a communication cable and such like, and connecting the imaging console 2 to a diagnostic console 3 as a case search apparatus via a communication network NT such as a LAN (Local Area Network). The apparatuses forming the case search system 100 are compliant with the DICOM (Digital Image and Communications in Medicine) standard, and the apparatuses are communicated with each other according to the DICOM.

[Configuration of Imaging Apparatus 1]

The imaging apparatus 1 performs imaging of a dynamic state in a subject which has cyclicity, such as the state change of inflation and deflation of a lung according to the respiration movement and the heartbeat, for example. The dynamic imaging means obtaining a plurality of images by repeatedly emitting a pulsed radiation such as X-ray to a subject at a predetermined time interval (pulse irradiation) or continuously emitting the radiation (continuous irradiation) at a low dose rate without interruption. In other words, dynamic imaging is the continuous radiographic imaging of the dynamic state of a target site having cyclicity along a time axis. Dynamic imaging may be performed using ultrasound or magnetism as well as radiation such as X-rays. Dynamic imaging includes imaging of moving image, but does not include taking still pictures while displaying a moving image.

A series of images obtained by the dynamic imaging is referred to as a dynamic image.

The dynamic image can be obtained by imaging using a semiconductor image sensor such as an FPD (Flat Panel Detector), for example.

The dynamic image includes a moving image, but does not include images obtained by imaging of still images while displaying a moving image.

Each of the plurality of images forming the dynamic image is referred to as a frame image. Hereinafter, embodiments will be described by taking, as an example, the dynamic imaging which is performed by the pulse irradiation. Though the following embodiments will be described by taking, as an example, the subject M which is a chest of a patient being tested, the present invention is not limited to this.

A radiation source 11 is located at a position facing a radiation detection unit 13 through a subject M, and emits radiation (X ray) to the subject M in accordance with control of an irradiation control apparatus 12.

The irradiation control apparatus 12 is connected to the imaging console 2, and performs radiographic imaging by controlling the radiation source 11 on the basis of an irradiation condition which was input from the imaging console 2. The irradiation condition input from the imaging console 2 is a pulse rate, a pulse width, a pulse interval, the number of imaging frames per imaging, a value of X-ray tube current, a value of X-ray tube voltage and a type of applied filter, for example. The pulse rate is the number of irradiation per second and consistent with an after-mentioned frame rate. The pulse width is an irradiation time required for one irradiation. The pulse interval is a time from start of one irradiation to start of next irradiation, and consistent with an after-mentioned frame interval.

The radiation detection unit 13 is configured by including a semiconductor image sensor such as an FPD. The FPD has a glass substrate, for example, and a plurality of detection elements (pixels) is arranged in matrix at a predetermined position on the substrate to detect, according to the intensity, radiation which was emitted from the radiation source 11 and has transmitted through at least the subject M, and convert the detected radiation into electric signals to be accumulated. Each pixel is formed of a switching section such as a TFT (Thin Film Transistor), for example. The FPD may be an indirect conversion type which converts X ray into an electrical signal by photoelectric conversion element via a scintillator, or may be a direct conversion type which directly converts X ray into an electrical signal. In one or more embodiments, a pixel value (signal value) of image data generated in the radiation detection unit 13 is a density value and higher as the transmission amount of the radiation is larger.

The radiation detection unit 13 is provided to face the radiation source 11 via the subject M.

The reading control apparatus 14 is connected to the imaging console 2. The reading control apparatus 14 controls the switching sections of respective pixels in the radiation detection unit 13 on the basis of an image reading condition input from the imaging console 2, switches the reading of electric signals accumulated in the pixels, and reads out the electric signals accumulated in the radiation detection unit 13 to obtain image data. The image data is a frame image. The reading control apparatus 14 outputs the obtained frame image to the imaging console 2. The image reading condition is, for example, a frame rate, frame interval, a pixel size and an image size (matrix size). The frame rate is the number of frame images obtained per second and consistent with the pulse rate. The frame interval is a time from start of obtaining one frame image to start of obtaining the next frame image, and consistent with the pulse interval.

Here, the irradiation control apparatus 12 and the reading control apparatus 14 are connected to each other, and transmit synchronizing signals to each other to synchronize the irradiation operation with the image reading operation.

[Configuration of Imaging Console 2]

The imaging console 2 outputs the irradiation condition and the image reading condition to the imaging apparatus 1, controls the radiographic imaging and reading operation of radiation images by the imaging apparatus 1, and displays the dynamic image obtained by the imaging apparatus 1 so that an imaging operator who performs the imaging such as an imaging operator confirms the positioning and whether the image is appropriate for diagnosis.

As shown in FIG. 1, the imaging console 2 is configured by including a controller 21, a storage 22, an operation unit 23, a display 24 and a communication unit 25, which are connected to each other via a bus 26.

The controller 21 is configured by including a CPU (Central Processing Unit), a RAM (Random Access Memory) and such like. According to the operation of the operation unit 23, the CPU of the controller 21 reads out instructions (e.g., system programs and various processing programs) stored in the storage 22 to load the instructions into the RAM, executes various types of processing including after-mentioned imaging control processing in accordance with the loaded instructions, and integrally controls the operations of the sections in the imaging console 2 and the irradiation operation and reading operation of the imaging apparatus 1.

The storage 22 is configured by including a non-volatile semiconductor memory, a hard disk or the like. The storage 22 stores various instructions executed by the controller 21, parameters necessary for executing processing by the instructions, and data of processing results. For example, the storage 22 stores instructions for executing the imaging control processing shown in FIG. 2. The storage 22 stores the irradiation condition and the image reading condition so as to be associated with the imaging site. The various instructions may be stored in a form of readable program code, and the controller 21 executes the operations according to the program code as needed.

The operation unit 23 is configured by including a keyboard including cursor keys, numeric keys and various function keys and a pointing device such as a mouse. The operation unit 23 outputs an instruction signal input by a key operation to the keyboard or a mouse operation to the controller 21. The operation unit 23 may include a touch panel on the display screen of the display 24. In this case, the operation unit 23 outputs the instruction signal which is input via the touch panel to the controller 21.

The display 24 is configured by a monitor such as an LCD (Liquid Crystal Display) and a CRT (Cathode Ray Tube), and displays instructions input from the operation unit 23, data and such like in accordance with an instruction of a display signal input from the controller 21.

The communication unit 25 includes a LAN adapter, a modem, a TA (Terminal Adapter) and such like, and controls the data transmission and reception with the apparatuses connected to the communication network NT.

[Configuration of Diagnostic Console 3]

The diagnostic console 3 obtains the dynamic image from the imaging console 2. The diagnostic console 3 displays the obtained dynamic image, generates a dynamic state analysis image by analyzing the obtained dynamic image, and searches for and outputs similar case images similar to the dynamic image or case candidates related to the dynamic image on the basis of the obtained dynamic image. Thus, the diagnostic console 3 is a case search apparatus that supports diagnosis by the doctor.

As shown in FIG. 1, the diagnostic console 3 is configured by including a controller 31 (hardware processor), a storage 32, an operation unit 33, a display 34 and a communication unit 35, which are connected to each other via a bus 36.

The controller 31 is configured by including a CPU, a RAM and such like. According to the operation of the operation unit 33, the CPU of the controller 31 reads out the instructions (e.g., system programs stored in the storage 32 and various processing programs) to load them into the RAM and executes the various types of processing in accordance with the loaded instructions. The CPU of the controller 31 reads out the instructions, e.g., a program 32a stored in the storage 32 to load the program 32a into the RAM, and executes after-mentioned case learning processing and case search processing according to the loaded program 32a.

The controller 31 searches by using the dynamic image, and outputs similar case images that are similar to the dynamic image or case candidates related to the dynamic image. The controller 31 functions as a controller.

The storage 32 is configured by including a nonvolatile semiconductor memory, a hard disk or the like. The storage 32 stores various instructions including the program 32a for executing the case learning processing and the case search processing by the controller 31, parameters necessary for executing processing by the instructions and data of processing results or the like. The various instructions may be stored in a form of readable program code, and the controller 31 executes the operations according to the program code as needed.

The storage 32 also stores a dynamic image which was obtained by dynamic imaging in the past or a dynamic state analysis image obtained by analyzing the dynamic image so as to be associated with an identification ID for identifying the dynamic image or the dynamic state analysis image, patient basic information, patient accompanying information, examination information, information on an image feature focused in the diagnosis, diagnosis result including the disease name, medical record information (chief complaint, objective information, etc.), medical history, label information for bookmark/conference, and etc. The diagnosis result is the result of diagnosing the dynamic image or the dynamic state analysis image. For example, the diagnosis results include the information which was input by a doctor after diagnosing an image, the information of a definite diagnosis obtained by pathological examination, and the result information of automatic analysis of a medical image using CAD or other methods.

The storage 32 also stores dynamic images or dynamic state analysis images obtained by imaging of multiple patients.

The storage 32 may store the dynamic image or the dynamic state analysis image obtained in the past so as to be associated with the information on the region of interest which was focused by the doctor in the diagnosis.

The storage 32 also stores a frame image group for one cycle of the dynamic state that is included in the dynamic image or the dynamic state analysis image, so as to be associated with the feature amounts which were calculated on the basis of the information on the image feature focused in the diagnosis from the frame image group, and the information on the group which was decided by machine learning on the basis of the feature amounts. The group mentioned here is a group obtained by dividing the frame image groups included in the dynamic image or the dynamic state analysis image into several groups on the basis of a predetermined criteria (e.g., feature amounts in the frame images).

Here, the information on image feature focused in the diagnosis is described. When a doctor performs diagnosis on the basis of the dynamic image or the dynamic state analysis image which was generated on the basis of the dynamic image, if there is an image feature such as a longer expiratory time compared to an inspiratory time, a longer respiratory time, less change in density and a bad movement of a diaphragm, for example, the doctor performs diagnosis focusing on the image feature. Thus, when the controller 31 of the diagnostic console 3 displays the dynamic image or the dynamic state analysis image thereof on the display 34, the diagnostic console 3 also displays a user interface for inputting or specifying information on the image feature focused on by the doctor. In the storage 32, there is stored the information on the image feature which was input or specified by the operation unit 33 from the user interface so as to be associated with the dynamic image.

In one or more embodiments, when the diagnosis target is ventilation, it is possible to input or specify, as the focused image feature, any of a ratio (or difference) between an expiratory time and an inspiratory time, a respiratory time, a density change amount, a movement amount of a diaphragm, and an average change amount of a density or the movement amount of the diaphragm in expiration and inspiration. When the diagnosis target is a pulmonary blood flow, it is possible to input or specify, as the focused image feature, a time of one cycle, a density change amount, an average change amount from a maximum to a minimum (or from a minimum to a maximum) of the density change in one cycle, and such like.

As the past dynamic image, there is stored a dynamic image formed of a frame image group for one cycle of the dynamic state which was used for diagnosis.

The operation unit 33 is configured by including a keyboard including cursor keys, numeric keys and various function keys and a pointing device such as a mouse, and outputs an instruction signal input by a key operation to the keyboard and a mouse operation to the controller 31. The operation unit 33 may include a touch panel on the display screen of the display 34. In this case, the operation unit 33 outputs an instruction signal, which was input via the touch panel, to the controller 31.

The display 34 is configured by including a monitor such as an LCD and a CRT, and performs various displays in accordance with the instruction of a display signal input from the controller 31.

The communication unit 35 includes a LAN adapter, a modem, a TA and such like, and controls data transmission and reception with the apparatuses connected to the communication network NT.

The dynamic state analysis image which is generated by analyzing the dynamic image is described here.

The dynamic state analysis image is an image generated by performing an analysis process to the dynamic image. The dynamic state analysis image is, for example, a blood flow analysis image in which the dynamic state of blood flow function is analyzed, a ventilation analysis image in which the dynamic state of ventilation function is analyzed, or an adhesion analysis image in which the dynamic state of adhesion is analyzed.

The analysis process in the dynamic state analysis image includes, for example, frequency filtering in the time direction. For example, if the diagnostic target is ventilation, a low-pass filtering process (e.g., cutoff frequency of 0.85 Hz) is applied to the density changes in the frame image group in the temporal direction. The dynamic state analysis image is generated by extracting the density changes caused by ventilation. For example, if the diagnostic target is pulmonary blood flow, a high-pass filtering process (e.g., cutoff frequency of 0.85 Hz) is applied to the frame image group in the temporal direction. The dynamic state analysis image is generated by extracting the density changes caused by the pulmonary blood flow. A bandpass filter (e.g., low cutoff frequency of 0.8 Hz, high cutoff frequency of 2.4 Hz) may be used to filter the density changes in the frame image group to extract the density changes due to pulmonary blood flow.

The analysis process may be performed by associating pixels in the same position of respective frame images in the frame image group to each other and applying frequency filtering in the time direction to each pixel. Each frame image in the frame image group may be divided into sub-regions consisting of multiple pixels, the representative value (e.g., mean value, median value, etc.) of the density values for each divided sub-region may be calculated, the divided sub-regions may be associated with each other between frame images (e.g., sub-regions at the same pixel position may be associated), and frequency filter processing in the time direction may be applied for each sub-region.

For each pixel (or each sub-region) of the frame image group to which the analysis process has been performed, the representative value (e.g., variance value) in the time direction may be obtained, and a single image with the obtained value as the pixel value may be generated as the dynamic state analysis image.

[Operation of Case Search System 100]

Next, the operation of the case search system 100 will be described.

(Operations of Imaging Apparatus 1 and Imaging Console 2)

First, imaging operation by the imaging apparatus 1 and the imaging console 2 will be described.

Figure 2:
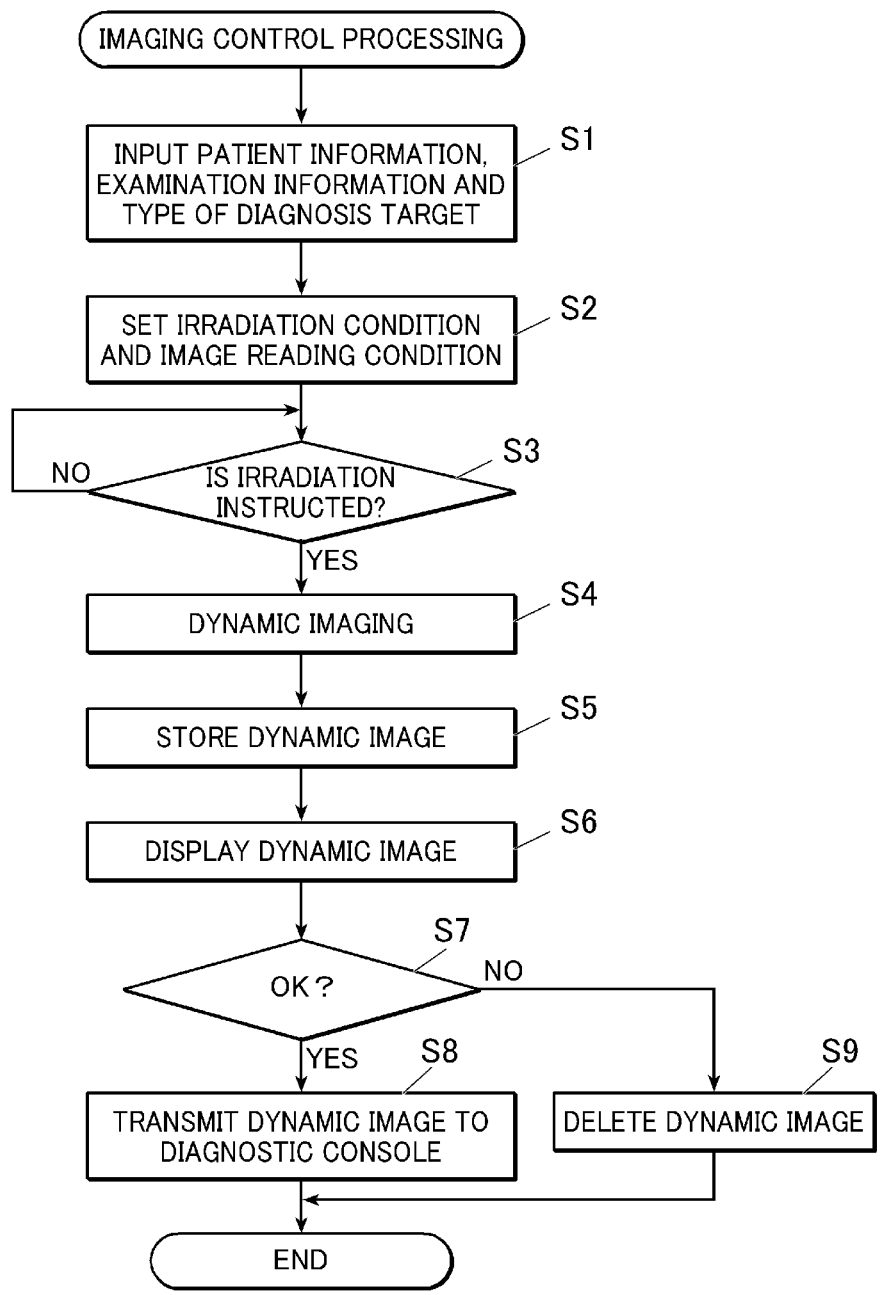
FIG. 2 is a flowchart showing imaging control processing executed by a controller of an imaging console in FIG. 1.

FIG. 2 shows imaging control processing executed by the controller 21 in the imaging console 2. The imaging control processing is executed in cooperation between the controller 21 and the instructions stored in the storage 22.

First, the controller 21 receives input of patient basic information for the patient being tested (patient name, height, weight, age, gender and such like) and examination information (imaging site (here, chest) and the type of the diagnosis target (ventilation, pulmonary blood flow or the like)) made by the imaging operator, via the operation unit 23 in the imaging console 2 (step S1).

Next, the controller 21 reads out the irradiation condition from the storage 22 and sets the irradiation condition in the irradiation control apparatus 12, and reads out the image reading condition from the storage 22 and sets the image reading condition in the reading control apparatus 14 (step S2).

Next, the controller 21 determines whether or not an instruction of irradiation by the imaging operator was made via the operation unit 23 (step S3). The imaging operator locates the subject M between the radiation source 11 and the radiation detection unit 13, and performs positioning. The imaging operator instructs the patient being tested to be at ease to lead into quiet breathing. The imaging operator may induce deep breathing by instructing "breathe in, breathe out", for example. When the diagnosis target is pulmonary blood flow, for example, the imaging operator may instruct the patient being tested to hold the breath since the image feature is obtained more easily when the imaging is performed while the patient holds the breath. When the preparation for imaging is completed, the imaging operator operates the operation unit 23 to input an irradiation instruction.

When the irradiation instruction is input from the operation unit 23 by the imaging operator (step S3: YES), the controller 21 outputs the imaging start instruction to the irradiation control apparatus 12 and the reading control apparatus 14, and starts the dynamic imaging (step S4). That is, radiation is emitted by the radiation source 11 at the pulse interval set in the irradiation control apparatus 12, and frame images are obtained by the radiation detection unit 13.

When the imaging is finished for a predetermined number of frames, the controller 21 outputs an instruction to end the imaging to the irradiation control apparatus 12 and the reading control apparatus 14, and stops the imaging operation. The imaging is performed to obtain the number of frame images which can capture at least one respiration cycle.

The controller 21 then stores the frame images obtained by the imaging in the storage 22 so as to be associated with respective numbers (frame numbers) indicating the imaging order (step S5).

Next, the controller 21 displays the frame images obtained by the imaging on the display 24 (step S6). The imaging operator confirms positioning and such like by the displayed dynamic image, and determines whether an image appropriate for diagnosis was acquired by the imaging (imaging was successful) or imaging needs to be performed again (imaging failed).

The controller 21 receives the input that the imaging was successful or that the imaging failed by the imaging operator via the operation unit 23, and determines whether or not the determination result indicating that the imaging was successful was input (step S7).

If the controller 21 has determined that the determination result indicating that the imaging was successful was input (step S7: YES), the controller 21 attaches, to each of a series of frame images obtained by the dynamic imaging in step S4, information such as the identification ID for identifying the dynamic image, the patient basic information, the examination information, the irradiation condition, the image reading condition and the number (frame number) indicating the imaging order (for example, the information is written into a header region of the image data in the DICOM format), and transmits it to the diagnostic console 3 via the communication unit 25 (step S8). Then, the controller 31 ends the processing. The controller 31 of the diagnostic console 3 receives the series of frame images obtained by dynamic imaging via the communication unit 35, and stores them in the storage 32.

On the other hand, if the controller 21 determines that the determination result indicating that the imaging failed was input (step S7: NO), the controller 21 deletes the series of frame images stored in the storage 22 (step S9), and ends the processing. In this case, the imaging needs to be performed again.

(Operation of Diagnostic Console 3)

The operation of the diagnostic console 3 will be described.

Figure 3:
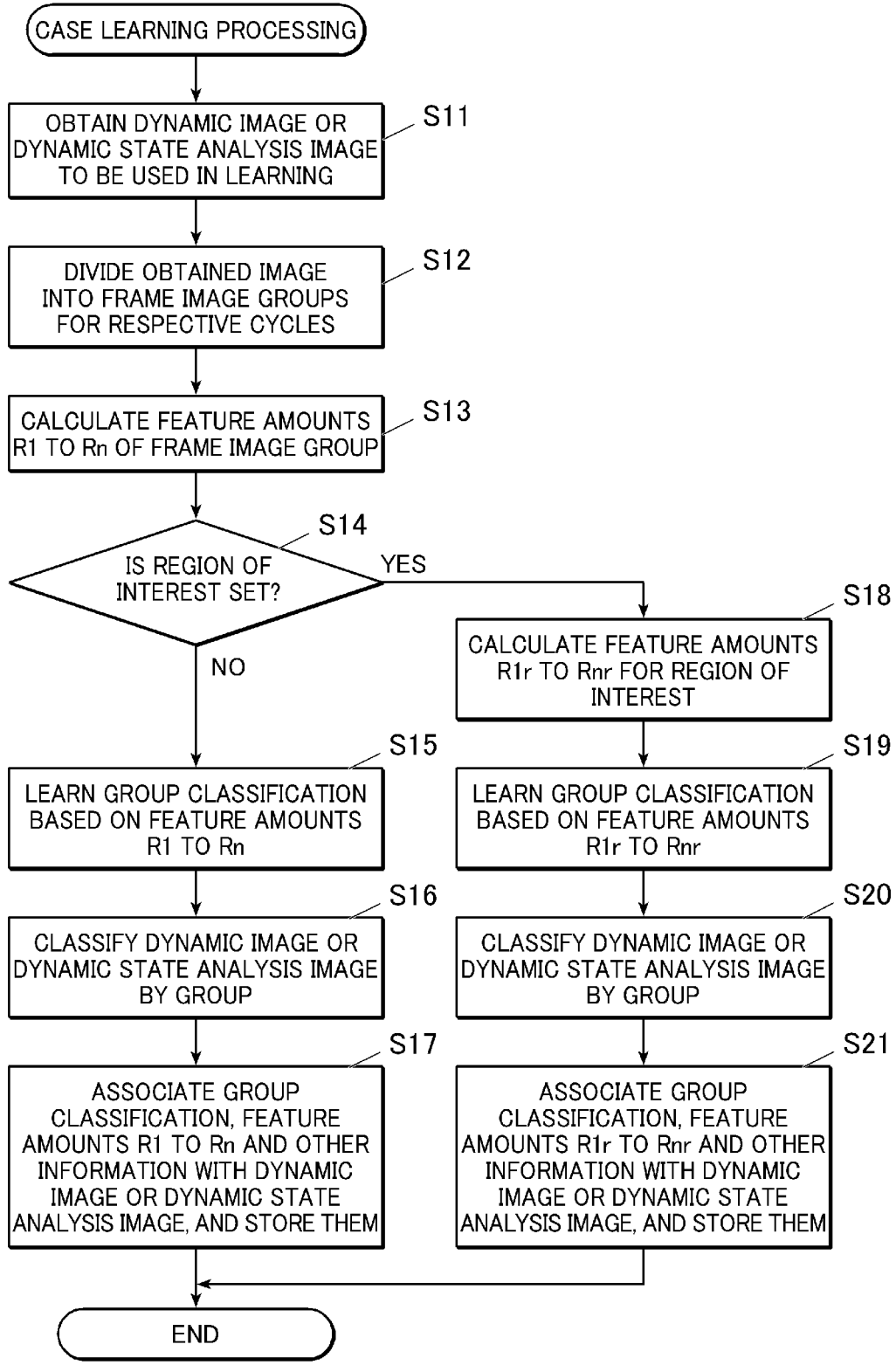
FIG. 3 is a flowchart showing case learning processing executed by a controller of a diagnostic console in FIG. 1.

The case learning processing shown in FIG. 3 will be first described.

The controller 31 executes the case learning processing in cooperation with the instructions, e.g., the program 32*a* stored in the storage 32, to learn group classification with the disease name as the correct answer for the dynamic image or the dynamic state analysis image stored in the storage 32.

The learning of group classification with the disease name as the correct answer for the dynamic image or the dynamic state analysis image is not limited to the example shown in FIG. 3, and may be performed by any other method.

Hereinafter, the flow of case learning processing will be described with reference to FIG. 3.

The controller 31 obtains the dynamic image or the dynamic state analysis image used in learning from the storage 32 (step S11).

Next, the controller 31 divides the obtained dynamic image or the dynamic state analysis image into frame image groups for respective cycles of the dynamic state (step S12).

Figure 4:
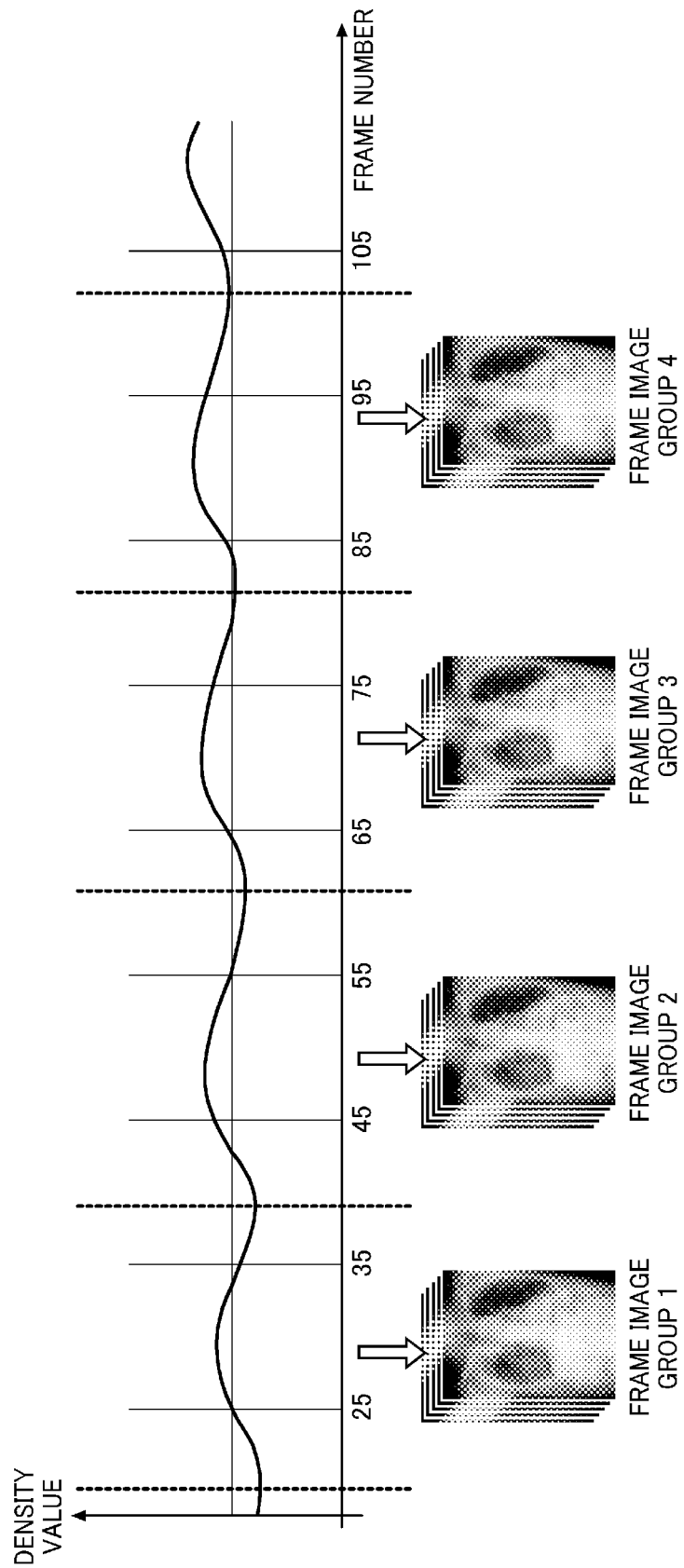
FIG. 4 is a view for explaining a method of dividing a dynamic image into multiple frame image groups.

In the division in step S12, for example, density change of the entire image is used. For example, a representative value (for example, average value, median value or the like) of the density values is calculated in each frame image of the dynamic image, and as shown in FIG. 4, a waveform of the density change is obtained by plotting the calculated representative values of the density values temporally (in the frame image order). The waveform is divided at frame images corresponding to local values (local maximum or local minimum), and thereby the dynamic image is divided into frame image groups for respective cycles of the dynamic state of the subject M. The dynamic image may be divided into frame image groups for respective cycles of the dynamic state by extracting the target site (for example, lung field region) from the dynamic image and using the density change in the extracted region.

For example, when the diagnosis target is ventilation, the division may be performed after the density change is subjected to low pass filter processing (for example, cutoff frequency is 0.85 Hz) in the time direction. Thus, it is possible to remove the signal change of high frequency caused by pulmonary blood flow and such like and accurately extract the density change caused by the ventilation.

For example, when the diagnosis target is pulmonary blood flow, the division may be performed after the density change is subjected to high pass filter processing (for example, cutoff frequency is 0.85 Hz) in the time direction. Thus, it is possible to remove the signal change of low frequency caused by ventilation and such like and accurately extract the density change caused by the pulmonary blood flow. The density change by the pulmonary blood flow may be extracted by using a band pass filter (for example, cutoff frequency of low range is 0.8 Hz and cutoff frequency of high range is 2.4 Hz).

When the diagnosis target is ventilation, the division into a plurality of frame image groups may be performed by using the change in the movement amount of the diaphragm. For example, in each frame image of the dynamic image, the diaphragm is recognized, the y coordinate at a position of an x coordinate on the recognized diaphragm is obtained, and the distance between the obtained y coordinate and a y coordinate which is a reference (for example, distance from the y coordinate at the resting expiration position or the distance between the obtained y coordinate and the lung apex) is plotted temporally. Thereby, a waveform of the temporal change in the movement amount of the diaphragm is obtained and divided at frame images corresponding to the local values (local maximum or local minimum) to divide the dynamic image into frame image groups (frame image groups 1 to n (n>1 and n is integer)) for respective cycles of the dynamic state of the subject. Here, the horizontal direction is referred to as x direction and the vertical direction is referred to as y direction in each of the frame images.

As for recognition of the diaphragm, for example, a lung field region is recognized from the frame image, and the outline of the lower section of the recognized lung field region can be recognized as the diaphragm. The lung field region may be extracted by any method. For example, a threshold value is obtained by a discriminant analysis from histogram of the signal value for each pixel of the frame image to recognize the lung field region, and the region having higher signals than the threshold value is primarily extracted as a lung field region candidate. Then, edge detection is performed around the border of the lung field region candidate which was primarily extracted, and the points having largest edges in sub-regions around the border are extracted along the border to extract the border of the lung field region.

The controller 31 obtains, from the storage 32, information on the image feature which is stored so as to be associated with the dynamic image or the dynamic state analysis image obtained in step S11. The controller 31 calculates the feature amounts R1 to Rn of the image feature on the basis of the obtained information on the image feature, for the respective frame image groups 1 to n that were divided in step S12 (step S13). In calculating the feature amounts R1 to Rn of the image feature, various such as histogram, gray value, pixel mean, center of gravity, entropy, edge, and contrast in frame image groups 1 to n may be used. The amounts of change in multiple biological sites (graph of change over time) obtained from the dynamic state analysis image may also be used.

As mentioned above, when the diagnosis target is ventilation, the image feature includes any of a ratio (or difference) between an expiratory time and an inspiratory time, a respiratory time, a density change amount, a movement amount of a diaphragm, and an average change amount of a density or the movement amount of the diaphragm in expiration and inspiration. When the diagnosis target is a pulmonary blood flow, the image feature includes any of the time of one cycle, a density change amount, an average change amount from a maximum to a minimum (or from a minimum to a maximum) of the density change in one cycle, and such like.

The feature amounts R1 to Rn of the above image feature can be calculated on the basis of the density changes or the movement amounts of the diaphragm in the frame image groups.

As for the ratio between an expiratory time and an inspiratory time, the expiratory time is obtained by calculating the time it takes for the density or the movement amount of the diaphragm to go from local maximum to local minimum in the frame image group, the inspiratory time is obtained by calculating the time it takes for the density or the movement amount of the diaphragm to go from local minimum to local maximum in the frame image group, and the ratio can be obtained by calculating the value of ratio between the expiratory time and the inspiratory time. The respiratory time can be obtained by adding the expiratory time and the inspiratory time.

The density change amount can be obtained by calculating the amplitude value of the density change in the frame image group.

The movement amount of diaphragm can be obtained by calculating amplitude value of the movement amount of diaphragm in the frame image group.

The time of one cycle of the pulmonary blood flow can be obtained by calculating the time it takes for the density of the frame image group to go from local maximum (local minimum) to the next local maximum (local minimum).

When the diagnosis target is ventilation, the feature amounts R1 to Rn may be calculated after the density change of each frame image group is subjected to low pass filter processing (for example, cutoff frequency is 0.85 Hz) in the time direction. By this, it is possible to remove the signal change of high frequency caused by pulmonary blood flow and such like and accurately extract the density change caused by the ventilation.

When the diagnosis target is pulmonary blood flow, the feature amounts R1 to Rn may be calculated after the density change of each frame image group is subjected to high pass filter processing (for example, cutoff frequency is 0.85 Hz) in the time direction. By this, it is possible to remove the signal change of low frequency caused by ventilation and such like and accurately extract the density change caused by the pulmonary blood flow. The density change by the pulmonary blood flow may be extracted by using a band pass filter (for example, cutoff frequency of low range is 0.8 Hz and cutoff frequency of high range is 2.4 Hz).

After extracting the pulmonary region from each frame image, the density change is calculated by using the pixels within the region. Thereby, it is possible to more accurately calculate the feature amounts R1 to Rn related to ventilation and pulmonary blood flow.

The controller 31 determines whether or not the region of interest in the dynamic image or the dynamic state analysis image is set in advance (step S14).

If the region of interest is not set (step S14; NO), the controller 31 learns group classification by performing machine learning on the basis of the feature amounts R1 to Rn which were calculated in step S13 (step S15). As for the machine learning in step S15, any known machine learning model may be used.

The controller 31 then classifies the dynamic image or the dynamic state analysis image which was obtained in step S11, by group, on the basis of the group classification learned in step S15 (step S16).

The controller 31 stores the dynamic image or the dynamic state analysis image which was classified in step S16 so as to be associated with the information on group classification, the feature amounts R1 to Rn, and other information, in storage 32 (step S17), and ends the processing. The above other information includes the identification ID which is stored so as to be associated with the dynamic image or the dynamic state analysis image, the patient basic information, the patient accompanying information, the examination information, the information on the image feature focused in the diagnosis, the disease name, medical record information (chief complaint, objective information, etc.), medical history, label information for bookmark/conference, and etc.

If the region of interest is set (step S14; YES), the controller 31 calculates the feature amounts R1r to Rnr of the image feature respectively for the region of interest r in the frame image groups 1 to n (step S18).

The controller 31 learns group classification by performing machine learning on the basis of the feature amounts R1r to Rnr which were calculated in step S18 (step S19). As for the machine learning in step S19, any known machine learning model may be used similarly to step S15.

The controller 31 then classifies, by group, the dynamic image or the dynamic state analysis image which was obtained in step S11 on the basis of the group classification learned in step S19 (step S20).

The controller 31 stores the dynamic image or the dynamic state analysis image which was classified in step S20 so as to be associated with the information on group classification, the feature amounts R1r to Rnr, and other information, in the storage 32 (step S21), and ends the processing.

The controller 31 executes the above case learning processing by using the dynamic images or the dynamic state analysis images obtained by imaging of multiple patients. When the group classification is learned for the dynamic image or the dynamic state analysis image by a method other than the above case learning processing, the dynamic images or the dynamic state analysis images obtained by imaging of multiple patients are also used.

In the case learning processing, the dynamic images or the dynamic state analysis images are learned for model of the machine learning. However, the present invention is not limited to this. Still images may be learned in addition to the dynamic images or the dynamic state analysis images.

As for the group in the group classification learned in steps S15, S19 in the above case learning processing, there may be different grouping according to the feature amount. To be specific, there may be grouping by the disease name, and the grouping further classifying the disease into Type I, II, III, IV, etc.

In the learning of group classification with the disease name as the correct answer, it is ideally desirable to preform classification so that the dynamic images or the dynamic state analysis images associated with information on a single disease name belong to one group. However, the dynamic images or the dynamic state analysis images associated with the information on one disease name may branch and belong to multiple groups.

Figure 5:
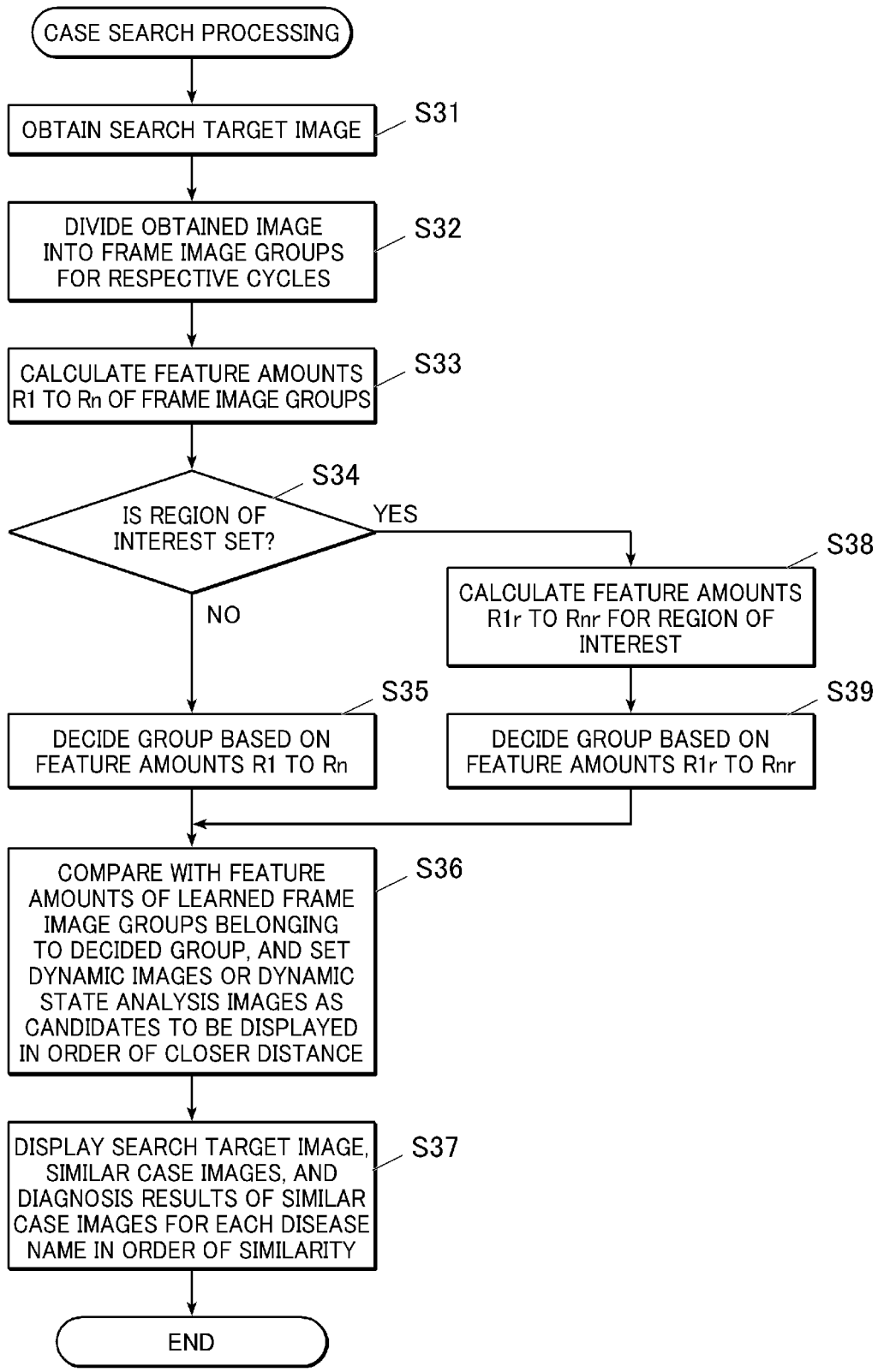
FIG. 5 is a flowchart showing case search processing executed by the controller of the diagnostic console in FIG. 1.

Next, the case search processing shown in FIG. 5 will be described.

When the search target image is selected by the user on the search screen 341 shown in FIG. 6 to be described later via the operation unit 33 of the diagnostic console 3 and the instruction to execute the search is made, the case search processing is executed by cooperation between the controller 31 and the program 32a stored in the storage 32. The search target image is the dynamic image used for the search. To be specific, the search target image is the image which is not yet diagnosed and the user intends to diagnose, among the dynamic images or the dynamic state analysis images stored in the storage 32.

When the user selects the search target image, the user may specify the region of interest which is the region to be focused in the diagnosis on the search screen 341.

Hereinafter, with reference to FIG. 5, the flow of case search processing will be described.

The controller 31 first obtains the dynamic image or the dynamic state analysis image which is the search target image selected by the user, from the storage 32 (step S31). The step S31 is the obtaining step (obtaining).

Next, the controller 31 divides the search target image which was obtained in step s31 into frame image groups for respective cycles of the dynamic state (step S32). The division in step S32 may be performed similarly to step S12 in the above case learning processing.

The controller 31 calculates the feature amounts R1 to Rn of the image feature for the respective frame image groups 1 to n that were divided in step S32 (step S33). Similarly to step S13 in the case learning processing, in calculating the feature amounts R1 to Rn of the image feature in step S33, various such as histogram, gray value, pixel mean, center of gravity, entropy, edge, and contrast in frame image groups 1 to n may be used. The amount of change in multiple biological sites (graph of change over time) obtained from the dynamic state analysis image may also be used.

The controller 31 determines whether or not the region of interest in the search target image is set (step S34).

If the region of interest is not set (step S34; NO), the controller 31 decides the group to which the search target image belongs by using, for example, the machine learning model learned in the case learning processing, on the basis of the feature amounts R1 to Rn calculated in step S33 (step S35).

The controller 31 then compares the feature amount Rn calculated in step S33 with the feature amount Ry of the frame image group y constituting the dynamic image or the dynamic state analysis image learned in the case learning processing and belonging to the group decided in step S35. The controller 31 sets each dynamic image or dynamic state analysis image consisting of the frame image group y corresponding to the feature amount Ry which has a close distance to the feature amount Rn in the feature amount space, as a display candidate in the order of closer distance, that is, in the order of similarity (step S36). The dynamic image or the dynamic state analysis image belonging to the group decided in step S35 is referred to as a similar case image which is similar to the search target image.

The controller 31 obtains the diagnosis result which is stored so as to be associated with the similar case image from the storage 32 as a case candidate, and refers to the diagnosis result for the disease name. The controller 31 then displays, on the display 34, the search target image, the similar case images, and the diagnosis results of the similar case images as the case candidates related to the search target image in the order of similarity for each disease name for which the controller 31 referred to the diagnosis result (step S37), and ends the processing. That is, the controller 31 outputs the similar case images similar to the search target image (dynamic image) and associated with the case candidate, and the case candidates related to the search target image (dynamic image).

The similar case image indicates the image which is output as the image of the case similar to that of the search target image (dynamic image). The similarity may be determined from the similarity of image itself, or the similarity may be determined from case information other than the image.

The steps S36 and S37 are search steps (searching).

If the region of interest is set (step S34; YES), the controller 31 calculates the feature amounts R1r to Rnr of the image feature respectively for the region of interest r in the frame image groups 1 to n (step S38). The steps S33 and S38 are the feature amount calculation steps (feature amount calculating).

The controller 31 decides the group to which the search target image belongs by using, for example, the machine learning model learned in the case learning processing, on the basis of the feature amounts R1r to Rnr calculated in step S38 (step S39).

The controller 31 then proceeds to step S36. In step S36, the controller 31 compares the feature amount Rnr calculated in step S38 with the feature amount Ryr of the region of interest r in the frame image group y constituting the dynamic image or the dynamic state analysis image learned in the case learning processing and belonging to the group decided in step S39. The controller 31 sets each dynamic image or dynamic state analysis image consisting of the frame image group y corresponding to the feature amount Ryr which has a close distance to the feature amount Rnr in the feature amount space, as a display candidate in the order of closer distance, that is, in the order of similarity. The dynamic image or the dynamic state analysis image belonging to the group decided in step S39 is referred to as a similar case image which is similar to the search target image.

Figure 6:
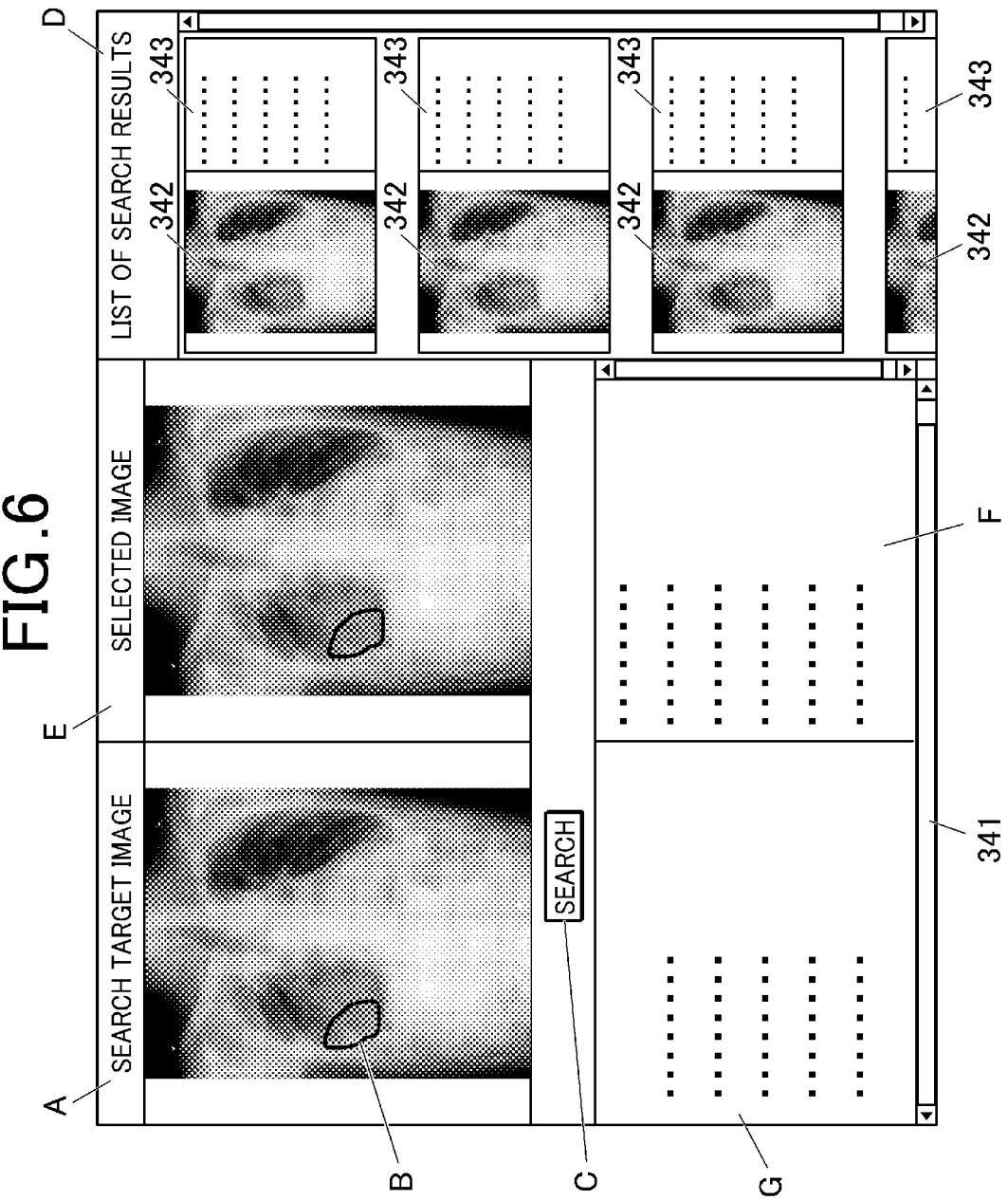
FIG. 6 is a view showing an example of a search screen displayed on a display of the diagnostic console in FIG. 1.

FIG. 6 shows an example of the search screen 341 which the controller 31 displays on the display 34 of the diagnostic console 3.

In the example shown in FIG. 6, the search target image selected by the user is displayed in the field A.

When the region of interest in the search target image is set in advance, the region is marked on the image by the region B. When the user can specify the region of interest on the search screen 341, the specified region may be displayed as the region B.

The button C is a search button, and the user can instruct to execute the search by pressing the button C.

In the field D, the similar case images 342 set as the display candidates in step S36 of the case search processing and their diagnosis results 343 are displayed in the order of similarity for each disease name. The user can refer to the similar case images associated with the information on the disease name for reference by selecting the disease name via the operation unit 33, and can compare the similar case images with the search target image.

In the field E, the similar case image selected from the field D via the operation unit 33 by the user is displayed.

In the field F, the diagnosis result of the similar case image displayed in the field E is displayed.

In the example shown in FIG. 6, the diagnosis result of the similar case image may not displayed in the field D, and only the similar case image may be displayed.

In the field D and the field F, there may be displayed not only the diagnosis result of each similar case image but also the identification ID, the patient basic information, the patient accompanying information, the examination information, the information on the image feature focused in the diagnosis, the disease name, medical record information (chief complaint, objective information, etc.), medical history, label information for bookmark/conference, and etc., which are associated with the similar case image.

In the field G, there may be displayed the identification ID, the patient basic information, the patient accompanying information, the examination information, the information on the image feature focused in the diagnosis, the disease name, medical record information (chief complaint, objective information, etc.), medical history, label information for bookmark/conference, and etc., which are associated with the search target image.

Modification Example

Hereinafter, a modification example will be described.

Since the configuration in the modification example and the operations of the imaging apparatus 1 and the imaging console 2 are similar to those described in one or more embodiments, the explanation is omitted and the operation of the diagnostic console 3 will be described.

Figure 7:
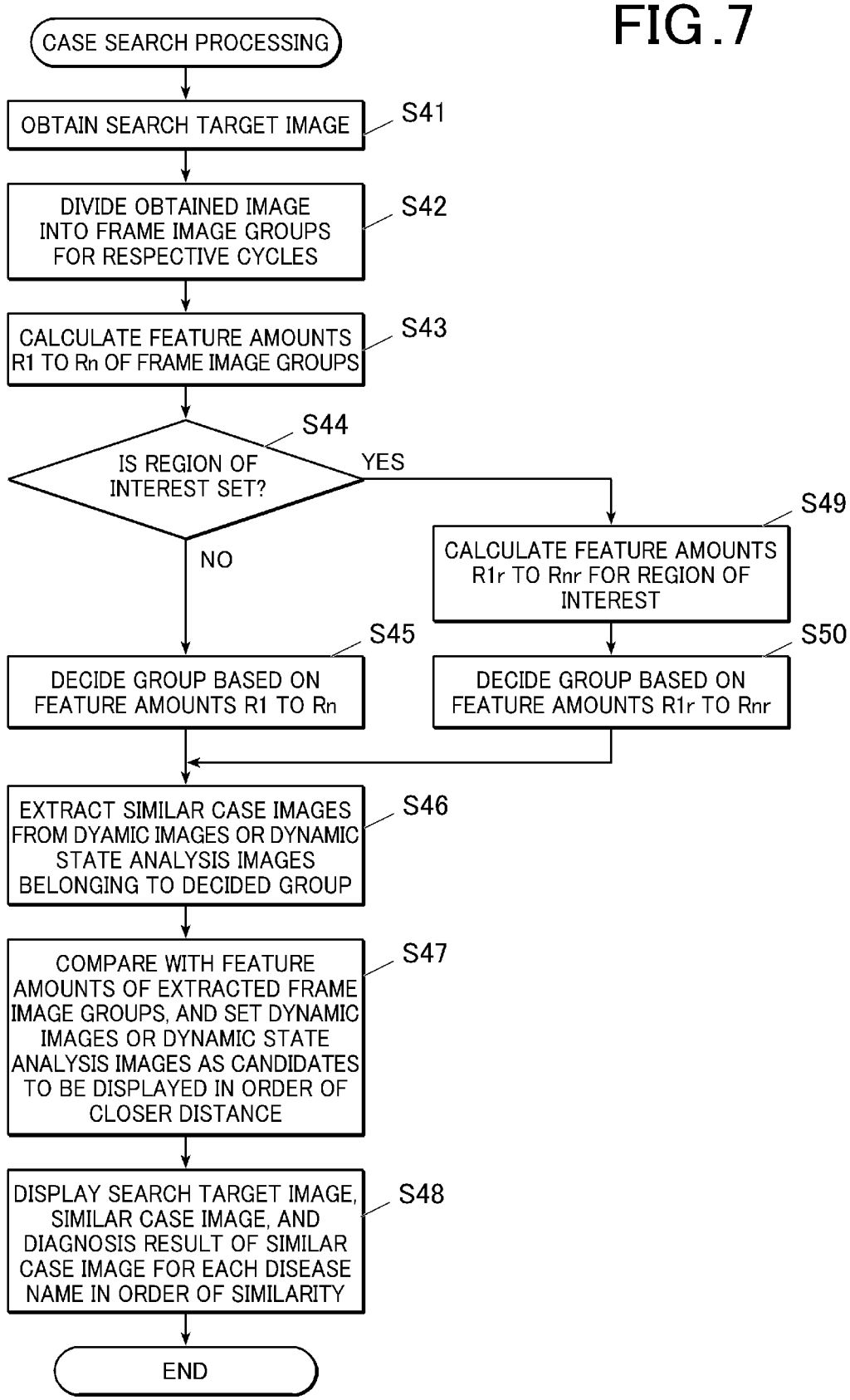
FIG. 7 is a flowchart showing case search processing executed by the controller of the diagnostic console in FIG. 1 in a modification example.

Hereinafter, with reference to FIG. 7, the flow of the case search processing in the modification example will be described.

The controller 31 first performs the steps S41 to S45 similar to the steps S31 to S35 in the case search processing in one or more embodiments.

Next, the controller 31 extracts dynamic images or dynamic state analysis images from, for example, the dynamic images or the dynamic state analysis images learned in the case learning processing, and belonging to the group decided in step S45, on the basis of the information associated with the search target image or the information associated with the learned dynamic image or dynamic state analysis image (step S46). To be specific, the controller 31 extracts the dynamic image or the dynamic state analysis image associated with the same patient basic information as the patient basic information associated with the search target image. The controller 31 extracts the dynamic image or the dynamic state analysis image associated with the information according to the conditions on which the user wants to search. The information according to the conditions on which the user wants to search is, for example, the identification ID, the patient basic information, the patient accompanying information, the examination information, the information on the image feature focused in the diagnosis, the diagnosis result including the disease name, medical record information (chief complaint, objective information, etc.), medical history, label information for bookmark/conference, etc. The extracted dynamic image or the dynamic state analysis image is referred to as a similar case image.

The controller 31 then compares the feature amount Rn calculated in step S43 with the feature amount Rz of the frame image group z constituting the dynamic image or the dynamic state analysis image extracted in step S46. The controller 31 sets each dynamic image or dynamic state analysis image consisting of the frame image group z corresponding to the feature amount Rz which has a close distance to the feature amount Rn in the feature amount space, as a display candidate in the order of closer distance, that is, in the order of similarity (step S47).

The controller 31 obtains the diagnosis result which is stored so as to be associated with each similar case image from the storage 32 as a case candidate, and refers to the diagnosis result for the disease name. The controller 31 then displays, on the display 34, the search target image, the similar case images, and the diagnosis results of the similar case images as the case candidates related to the search target image in the order of similarity for each disease name for which the diagnosis result was referred to (step S48), and ends the processing. That is, the controller 31 outputs the similar case images similar to the search target image (dynamic image) and associated with the case candidate, and the case candidates related to the search target image (dynamic image).

The similar case image indicates the image which is output as an image of the case similar to that of the search target image (dynamic image). The similarity may be determined from the similarity of image itself, or the similarity may be determined from case information other than the image.

The steps S46 to S48 are search steps (searching).

If the region of interest is set (step S44; YES), the controller 31 performs the steps S49 and S50 similar to those of steps S38 and S39 in the case search processing in one or more embodiments.

By performing the step S46 of the case search processing in the modification example, it is possible to narrow down the similar case images as display candidates, which enables to shorten the processing time in steps S47 and S48.

The search target image and the similar case image may consist of the frame image group (multiple frame images) forming the dynamic image, or may consist of a single frame image. That is, search target image and the similar case image may consist of at least one frame image forming the dynamic image. When the search target image and the similar case image consist of a single frame image, it is possible to execute the case search by using one frame image among the multiple frame images forming the dynamic image having a larger amount of information than that of the still image. Thus, it is possible to perform more accurate case search. When the search target image and the similar case image consist of multiple frame images, it is possible to execute the case search by using multiple frame images among the multiple frame images forming the dynamic image having a larger amount of information than that of the still image. Thus, it is possible to perform even more accurate case search.

When the search target image and the similar case image consist of the frame image group (multiple frame images) forming the dynamic image, the frame image group is consecutive frame images.

The search target image and the similar case image may be the image of a region of interest in one frame image forming the dynamic image. In this case, by performing the case search for the region of interest which was set in the frame image, it is possible to perform more accurate case search.

The search target image and the similar case image may be only a part of frame images among the multiple frame images forming the dynamic image. In this case, it is possible to execute the case search by using a part of frame images among the multiple frame images forming the dynamic image having a larger amount of information than that of the still image. Thus, it is possible to perform more accurate case search.

When the search target image and the similar case image consist of a single frame image forming the dynamic image, the single frame image may be selected by the user. This enables to execute the case search by using the frame image which was determined to be most suitable by the user, and thus it is possible to perform more accurate case search.

In the steps S37 and S48 of the case search processing, the search target image, the similar case images, and the diagnosis results of the similar case images are displayed in the order of similarity for each disease name. However, the present invention is not limited to this. Only the search target image and the disease names of the similar case images may be displayed, or only the search target image and the similar case images may be displayed.

That is, the controller 31 controls to display (output) the similar case image which is similar to the search target image and associated with the case candidate or the disease name of the similar case image which is the case candidate related to the search target image. At least one of the similar case image and the case candidate related to the case target image may be output. That is, any one of the similar case image and the case candidate related to the search target image may be output or both of them may be output.

The controller 31 may output multiple similar case images or case candidates related to the search target image, or only one similar case image or case candidate related to the search target image may be output. By outputting multiple similar case images or case candidates related to the search target image, the doctor can refer to more information to help make a diagnosis.

The controller 31 may display the search target image, the similar case images, and the diagnosis results of the similar case images in the order of similarity without dividing them by the disease name.

Though the machine-learned model which is used for the case search processing is described to be learned by the above case learning processing, the present invention is not limited to this. The case search processing may be performed by using external machine-learned model.

There may be used, for the case search processing, the model obtained by learning, additionally to the machine-learned model, the dynamic image which was taken by the imaging control processing or the dynamic state analysis image which was generated on the basis of the dynamic image. The dynamic image or the dynamic state analysis image used in the additional learning may be weighted more to be learned than the other dynamic image or the dynamic state analysis image. The weighted dynamic image or the dynamic state analysis image is learned in the machine learning model so that the search frequency is high at the time of case search processing. The weighting is made, for example, when the diagnosis result made with reference to the output result of the case search processing is different from definitive diagnosis (medical records and pathology) and additional learning is performed by using the definitive diagnosis, when additional learning is performed by using the diagnosis result by a specific doctor who are considered to be a great doctor, when additional learning is performed for the dynamic image or the dynamic state analysis image for which multiple doctors requested detailed view a large number of times and its diagnosis result, as a case which can be easily mistaken, and the case is used to perform the additional learning, and etc.

As for the region of interest which is set in advance in the dynamic image or the dynamic state analysis image in one or more embodiments and the modification example, a single region of interest may be set or multiple regions of interest may be set in the frame image.

In step S36 of the case search processing, the dynamic image or the dynamic state analysis image belonging to the group decided in step S35 was set as the similar case image which is similar to the search target image. In step S46 in the modification example of the case search processing, the dynamic image or the dynamic state analysis image is extracted from the learned dynamic image or dynamic state analysis image belonging to the group decided in step S45 on the basis of predetermined information, and the extracted dynamic image or the dynamic state analysis image was set as the similar case image. However, the present invention is not limited to this. Not only the dynamic image or the dynamic state analysis image belonging to the same group as the search target image, but also the dynamic image or the dynamic state analysis image which has a close distance of the feature amount and belonging to the adjacent group may be set as the similar case image. This enables to search many dynamic images or the dynamic state analysis images which have similar image feature but are associated with the information on different disease name.

In the case search processing, the dynamic image or the dynamic state analysis image selected by the user as the search target image may have the clear lesion area in the image. By using the dynamic image or the dynamic state analysis image which has the clear legion area in the case search processing, it is possible to perform accurate search.

In one or more embodiments and the modification example, the dynamic image is the image obtained by imaging using radiation, ultrasound, magnetism, etc. However, the dynamic image used in the case learning processing and the case search processing may be the image obtained by imaging using radiation. Since radiation is the most commonly used primary screening method for clinics and other facilities that perform dynamic imaging, the volume of dynamic images from radiation taken in the past is the largest. By the case search processing using the model obtained by machine learning of the dynamic images by radiation taken in the past, it is possible to perform more accurate case search.

Since the dynamic state analysis image used in one or more embodiments and the modification example includes the result of analysis processing as described above, the dynamic state analysis image has a larger amount of information than the dynamic image. Thus, it is possible to perform more accurate search by executing the case search processing with the dynamic state analysis image.

The dynamic images or the dynamic state analysis images obtained by imaging of multiple patients are used in learning of machine learning model which has learned group classification and which is used in steps S35 and S45 in the case search processing. Thus, in steps S37 and S48 of the case search processing, it is possible to display the similar case image obtained by imaging of patient different from the patient captured in the search target image or the diagnosis result of the different patient as the case candidate related to the search target image. That is, since it is possible to output the image or diagnosis result of different patient as the search result, the doctor can refer to more information.

In the case search processing, the similar case image is the dynamic image or the dynamic state analysis image. However, the still image (still picture) may be displayed as the similar case image.

The diagnostic console 3 may have a function of allowing the user to select the dynamic image or the dynamic state analysis image, the still image, or both of the dynamic image or the dynamic state analysis image and the still image, as the similar case image which is output in the case search processing.

As described above, the instructions for causing the case search apparatus to perform case search cause the controller 31 (computer) of the diagnostic console 3 (case search apparatus) to perform search step (step S36, S37, S46 to S48) that is performing search by using the dynamic image and outputting the similar case image similar to the dynamic image or the case candidate related to the dynamic image.

Accordingly, by using the dynamic image having a larger amount of information than that of the still image, it is possible to execute the case search using more information, and thus perform more accurate case search.

The controller 31 of the diagnostic console 3 performs obtaining step (steps S31, S41) that is obtaining the dynamic image, and the feature amount calculation step (step S33, S38, S43, S49) that is calculating the feature amount of the first image from the dynamic image obtained by the obtaining step. In the search step, the controller 31 performs control to output the similar case image similar to the dynamic image or the case candidate related to the dynamic image on the basis of the feature amount of first image (feature amount Rn, Rnr) which was calculated in the feature amount calculation step and the feature amount of the second image (feature amount Ry, Ryr) which was calculated by learning multiple frame images of the arbitrary dynamic image in advance.

Accordingly, it is possible to perform more accurate case search on the basis of the dynamic image which was taken in the past.

The dynamic image used in search in the case search executed by the controller 31 of the diagnostic console 3 is at least one frame image among multiple frame images forming the dynamic image.

Accordingly, by using the frame image forming the dynamic image which has a larger amount of information than that of the still image, it is possible to perform more accurate case search.

The dynamic image used in search in the case search executed by the controller 31 of the diagnostic console 3 is the image of the region of interest in at least one frame image among multiple frame images forming the dynamic image.

Accordingly, it is possible to perform more accurate case search for the region of interest which was set in the frame image.

In the case search executed by the controller 31 of the diagnostic console 3, the region of interest is the region specified by the user.

Accordingly, it is possible to execute the case search for the region of interest which the user determined to be most suitable, and thus it is possible to perform more accurate case search.

In the case search executed by the controller 31 of the diagnostic console 3, the dynamic image used in search is multiple frame images forming the dynamic image.

Accordingly, since the search target image is multiple frame images, it is possible to execute the case search by suing more information, and thus it is possible to perform more accurate case search.

In the case search executed by the controller 31 of the diagnostic console 3, the dynamic image used in search is a single frame image forming the dynamic image.

Accordingly, since the case search can be performed by using one frame image among multiple frame images forming the dynamic image which has a larger amount of information than that of the still image, it is possible to perform more accurate case search.

In the case search executed by the controller 31 of the diagnostic console 3, the dynamic image used in search is the image of the region of interest in one frame image forming the dynamic image.

Accordingly, it is possible to perform more accurate case search for the region of interest which was set in the frame image.

In the case search executed by the controller 31 of the diagnostic console 3, the dynamic image used in search is only a part of the multiple frame images forming the dynamic image.

Accordingly, since the case search can be performed by using a part of multiple frame images forming the dynamic image which has a larger amount of information than that of the still image, it is possible to perform more accurate case search.

In the case search executed by the controller 31 of the diagnostic console 3, the dynamic image used in search is the image selected by the user among multiple frame images forming the dynamic image.

Accordingly, it is possible to execute the case search for the image which the user determined to be most suitable to be used in the search, and thus it is possible to perform more accurate case search.

In the case search executed by the controller 31 of the diagnostic console 3, the dynamic image used in search is consecutive frame images among multiple frame images forming the dynamic image.

Accordingly, since the search target image is consecutive frame images, it is possible to execute the case search by using more information, and thus it is possible to perform more accurate case search.

In the case search executed by the controller 31 of the diagnostic console 3, the dynamic image is an image obtained by continuous radiographic imaging along a time axis of the dynamic state of the target site.

Accordingly, by using the dynamic image having a larger amount of information that that of the still image, it is possible to execute the case search by using more information, and thus it is possible to perform more accurate case search.

In the case search executed by the controller 31 of the diagnostic console 3, the dynamic image is an image obtained by continuous radiographic imaging along a time axis of the dynamic state of the target site having a cyclicity.

Accordingly, by using the dynamic image having a larger amount of information that that of the still image, it is possible to execute the case search by using more information, and thus it is possible to perform more accurate case search.

In the case search executed by the controller 31 of the diagnostic console 3, the dynamic image used in search is the dynamic state analysis image obtained by analyzing the dynamic image.

Accordingly, by using the dynamic state analysis image having a larger amount of information, it is possible to execute the case search by using more information, and thus it is possible to perform more accurate case search.

In the case search executed by the controller 31 of the diagnostic console 3, the dynamic state analysis image is any of a blood flow analysis image in which the dynamic state of blood flow function is analyzed, a ventilation analysis image in which the dynamic state of ventilation function is analyzed, and an adhesion analysis image in which the dynamic state of adhesion is analyzed.

Accordingly, by using the blood flow analysis image, the ventilation analysis image, or the adhesion analysis image having a larger amount of information, it is possible to execute the case search by using more information, and thus it is possible to perform more accurate case search.

In the case search executed by the controller 31 of the diagnostic console 3, the similar case image is the dynamic image.

Accordingly, it is possible to obtain more information more information as the case search result by outputting the dynamic image having a larger amount of information than that of the still image as the similar case image.

In the case search executed by the controller 31 of the diagnostic console 3, the similar case image is at least one frame image among multiple frame images forming the dynamic image.

Accordingly, it is possible to obtain more information more information as the case search result by outputting the frame images that form the dynamic image having a larger amount of information than that of the still image as the similar case image.

In the case search executed by the controller 31 of the diagnostic console 3, the similar case image is an image obtained by continuous radiographic imaging along a time axis of the dynamic state of the target site.

Accordingly, it is possible to obtain more information as the case search result by outputting the dynamic image having a larger amount of information than that of the still image as the similar case image.

In the case search executed by the controller 31 of the diagnostic console 3, the similar case image is an image obtained by continuous radiographic imaging along a time axis of the dynamic state of the target site having a cyclicity.

Accordingly, it is possible to obtain more information as the case search result by outputting the dynamic image having a larger amount of information than that of the still image as the similar case image.

In the case search executed by the controller 31 of the diagnostic console 3, the similar case image is the dynamic state analysis image obtained by analyzing the dynamic image.

Accordingly, by outputting the dynamic state analysis image having a larger amount of information as the similar case image, it is possible to obtain more information as the case search result.

In the case search executed by the controller 31 of the diagnostic console 3, the dynamic state analysis image is any of a blood flow analysis image in which the dynamic state of blood flow function is analyzed, a ventilation analysis image in which the dynamic state of ventilation function is analyzed, and an adhesion analysis image in which the dynamic state of adhesion is analyzed.

Accordingly, by outputting the blood flow analysis image, the ventilation analysis image, or the adhesion analysis image having a larger amount of information as the similar case image, it is possible to obtain more information as the case search result.

In the case search executed by the controller 31 of the diagnostic console 3, in the search step, multiple similar case images similar to the dynamic image or multiple case candidates related to the dynamic image are output.

Accordingly, the doctor can refer to more information to help make a diagnosis.

In the case search executed by the controller 31 of the diagnostic console 3, in the search step, the similar case images similar to the dynamic image or the case candidates related to the dynamic image are output in the order of similarity.

Accordingly, it is possible to refer to the similar case image which is more similar to the search target image.

In the case search executed by the controller 31 of the diagnostic console 3, in the search step, the similar case images similar to the dynamic image or the case candidates related to the dynamic image are output for each disease name.

Accordingly, it is possible to perform more accurate case search with the disease name as a reference.

In the case search executed by the controller 31 of the diagnostic console 3, in the search step, the similar case images similar to the dynamic image or the case candidates related to the dynamic image are output for each disease name in the order of similarity.

Accordingly, it is possible to perform more accurate case search with the disease name as a reference and refer to the similar case image which is more similar to the search target image.

The above description is an example of a case search system according to one or more embodiments of the present invention, and the present invention is not limited to this.

For example, in the above embodiments, the present invention is applied to the dynamic image of the chest as an example. However, the present invention is not limited to this. The present invention may be applied to the dynamic image obtained by imaging of other sites.

The storage 32 of the diagnostic console 3 in the above embodiments and modification example may store diagnosed images and diagnostic reports diagnosed by the imaging diagnostic physician or clinician in all diseases. By this, it is possible to use the images and diagnostic reports when providing education to residents, students, etc.

The storage 32 of the diagnostic console 3 in the above embodiments and modification example may store electronic medical books which is the practical reference books in the electronic form for imaging diagnostic physician. When the user fills out a diagnostic report, the electronic medical book may be configured to be viewed by displaying said electronic medical book on the display 34. It is desirable to have a configuration that the user can perform keyword search in the electronic medical book.

Moreover, for example, the above description discloses an example of using a hard disk, a semiconductor nonvolatile memory, etc. as a computer readable medium of the instructions according to one or more embodiments of the present invention, but the medium is not limited to this example. As other computer readable medium, portable recording media such as CD-ROM can be applied. Carrier wave is also applicable as a medium to provide the data of the instructions according to one or more embodiments of the present invention via communication lines.

As for the other detailed configurations and the detailed operations of the apparatuses forming the case search system 100, modifications can be made within the scope of the present invention.

According to one or more embodiments of the present invention, it is possible to perform more accurate search.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A non-transitory computer-readable storage medium storing instructions causing a computer of a case search apparatus to:
    obtain a dynamic image,
    execute a case search using the dynamic image,
    calculate a feature amount of a first image from the dynamic image, and
    output at least one of a similar case image similar to the dynamic image and a case candidate based on the feature amount of the first image and a feature amount of a second image calculated in advance by learning multiple frame images in an arbitrary dynamic image.

2. The non-transitory computer-readable storage medium according to claim 1, wherein the dynamic image used in the case search is at least one frame image among multiple frame images in the dynamic image.

3. The non-transitory computer-readable storage medium according to claim 2, wherein the dynamic image used in the case search is an image of a region of interest in the at least one frame image among the multiple frame images in the dynamic image.

4. The non-transitory computer-readable storage medium according to claim 3, wherein the region of interest is a region specified by a user.

5. The non-transitory computer-readable storage medium according to claim 2, wherein the dynamic image used in the case search is multiple frame images in the dynamic image.

6. The non-transitory computer-readable storage medium according to claim 2, wherein the dynamic image used in the case search is one frame image in the dynamic image.

7. The non-transitory computer-readable storage medium according to claim 2, wherein the dynamic image used in the case search is an image of a region of interest in one frame image in the dynamic image.

8. The non-transitory computer-readable storage medium according to claim 2, wherein the dynamic image used in the case search is only a part of the multiple frame images in the dynamic image.

9. The non-transitory computer-readable storage medium according to claim 2, wherein the dynamic image used in the case search is an image selected by a user among the multiple frame images in the dynamic image.

10. The non-transitory computer-readable storage medium according to claim 2, wherein the dynamic image used in the case search is consecutive frame images among the multiple frame images in the dynamic image.

11. The non-transitory computer-readable storage medium according to claim 1, wherein the dynamic image is an image obtained by continuous radiographic imaging along a time axis of a dynamic state of a target site.

12. The non-transitory computer-readable storage medium according to claim 1, wherein the dynamic image is an image obtained by continuous radiographic imaging along a time axis of a dynamic state of a target site having a cyclicity.

13. The non-transitory computer-readable storage medium according to claim 1, wherein the dynamic image used in the case search is a dynamic state analysis image in which the dynamic image is analyzed.

14. The non-transitory computer-readable storage medium according to claim 13, wherein the dynamic state analysis image is any one of: a blood flow analysis image in which a dynamic state of a blood flow function is analyzed; a ventilation analysis image in which a dynamic state of a ventilation function is analyzed; and an adhesion analysis image in which a dynamic state of adhesion is analyzed.

15. The non-transitory computer-readable storage medium according to claim 1, wherein the similar case image is a dynamic image.

16. The non-transitory computer-readable storage medium according to claim 15, wherein the similar case image is at least one frame image among multiple frame images in the dynamic image.

17. The non-transitory computer-readable storage medium according to claim 15, wherein the similar case image is an image obtained by continuous radiographic imaging along a time axis of a dynamic state of a target site.

18. The non-transitory computer-readable storage medium according to claim 15, wherein the similar case image is an image obtained by continuous radiographic imaging along a time axis of a dynamic state of a target site having a cyclicity.

19. The non-transitory computer-readable storage medium according to claim 15, wherein the similar case image is a dynamic state analysis image in which the dynamic image is analyzed.

20. The non-transitory computer-readable storage medium according to claim 19, wherein the dynamic state analysis image is any one of: a blood flow analysis image in which a dynamic state of a blood flow function is analyzed; a ventilation analysis image in which a dynamic state of a ventilation function is analyzed; and an adhesion analysis image in which a dynamic state of adhesion is analyzed.

21. The non-transitory computer-readable storage medium according to claim 1, wherein the instructions cause the computer to output at least one of: multiple similar case images similar to the dynamic image, and multiple case candidates related to the dynamic image.

22. The non-transitory computer-readable storage medium according to claim 1, wherein the instructions cause the computer to output at least one of the similar case image and the case candidate in order of similarity.

23. The non-transitory computer-readable storage medium according to claim 21, wherein the instructions cause the computer to output at least one of the similar case image and the case candidate for each disease name.

24. The non-transitory computer-readable storage medium according to claim 23, wherein the instructions cause the computer to output at least one of the similar case image and the case candidate in order of similarity for each disease name.

25. A case search apparatus comprising:
a hardware processor that:
obtains a dynamic image,
executes a case search using the dynamic image,
calculates a feature amount of a first image from the dynamic image, and
outputs at least one of a similar case image similar to the dynamic image and a case candidate based on the feature amount of the first image and a feature amount of a second image calculated in advance by learning multiple frame images in an arbitrary dynamic image.

* * * * *